(12) United States Patent
Matsumoto et al.

(10) Patent No.: US 6,636,316 B1
(45) Date of Patent: Oct. 21, 2003

(54) SPECTROSCOPIC METHOD FOR ANALYZING A GAS BY USING LASER BEAM

(75) Inventors: Koh Matsumoto, Tokyo (JP); Jie Dong, Tokyo (JP); Hiroshi Masusaki, Tokyo (JP); Katsumasa Suzuki, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 0 days.

(21) Appl. No.: 09/472,251

(22) Filed: Dec. 27, 1999

(51) Int. Cl.$^7$ ............................................... G01N 21/00
(52) U.S. Cl. ...................................................... 356/437
(58) Field of Search ................................. 356/436–440; 250/343, 339.13, 339.09

(56) References Cited

U.S. PATENT DOCUMENTS 6,040,915 A * 3/2000 Wu et al. ..................... 356/435

FOREIGN PATENT DOCUMENTS

JP        10-281988        10/1998

OTHER PUBLICATIONS

J.H. Park, et al.; "Atlas of Absorption Lines From 0 to 17900 cm$^{-1}$"; *NASA Reference Publication 118,81987*; pp. 1–2.

* cited by examiner

Primary Examiner—Frank G Font
Assistant Examiner—Amanda Merlino
(74) Attorney, Agent, or Firm—Merchant & Gould P.C.

(57) ABSTRACT

The present invention provides a spectroscopic method for analysing objects in a gas comprising a main ingredient and the objects, both of which the absorption spectra exist in the same wavelength range, with high precision and sensitivity by using a compact and simple single cell system.

In accordance with an aspect of the present invention, there is disclosed a spectroscopic method for analysing objects in a sample gas using a laser beam comprising: i) a step of splitting a laser beam into a first laser beam and a second laser beam; ii) a step of transmitting said first laser beam into a sample cell where a sample gas is introduced, and measuring an intensity of a spectrum of said transmitted first laser beam; iii) a step, being performed while performing said step ii), of transmitting said second laser beam into a reference cell where a reference gas is introduced, and measuring an intensity of a spectrum of said transmitted second laser beam, wherein said reference gas comprises an ingredient having at least two spectral lines of which wavelengths in an absorption spectrum of said reference gas are already known; and iv) a step of identifying a wavelength of objects to be measured in said sample gas by comparing said spectrum of sample gas with said spectrum of reference gas using said at least two spectral lines of said reference gas as reference wavelengths.

9 Claims, 7 Drawing Sheets

SPECTROSCOPIC METHOD FOR ANALYZING A GAS BY USING LASER BEAM

FIELD OF THE INVENTION

The present invention relates to a spectroscopic method for measuring absorption spectrum of a gas to be measured (hereinafter, "sample gas") using laser diode beam, for identifying impurities (hereinafter, also referred to as "objects (to be measured)") in the gas and for analyzing abundance ratio and concentration of the identified objects from the absorption spectrum with high precision and high sensitivity. Particularly the present invention relates to a spectroscopic method for analysing impurities in the gas, which includes main ingredient and impurities, with high precision and high sensitivity where it is difficult to take an absorption spectrum of the impurities due to the interference absorption of the main ingredient because the absorption spectra of the main ingredient and the impurities are in similar wavelength range.

BACKGROUND OF THE INVENTION

As a conventional spectroscopic method for analysing a small quantity of impurities in a gas with relatively good precision and sensitivity, a spectroscopic analysis method for measuring absorbance of laser diode has been used. However, it is very difficult to analyse a gas with high precision and sensitivity in which the absorption spectrum of the object to be measured is overlapped on the spectrum of the main ingredient, and the quantity of the object is in PPB($1/10^9$) level, as in the case of absorption spectra of ammonia $NH_3$ and water vapor $H_2O$, shown in FIG. 6. For example, it is very difficult to analyse the gas of which the object to be measured is water vapor and the main ingredient is a polyatomic molecule, such as ammonia $NH_3$ (or silane $SiH_4$).

Therefore, in order to analyse a gas including a main ingredient and impurities, such as water vapor, the inventors of the present invention have developed and filed a Japanese patent application No. HEI09-91158 of "An apparatus and a method for spectroscopic analysis using dual cell system". A schematic diagram of an embodiment of the dual cell system is shown in FIG. 7, where the apparatus comprises a sample cell 52 into which a sample gas G is introduced and a cancel cell 53 into which a cancel gas C, consisted of the main ingredient of the sample gas G without the impurities in the sample gas G, is introduced.

According to the above method and apparatus shown in FIG. 7, a laser beam L from a laser source 51 is splitted into laser beams L1 and L2 by the beam splitter 54, and the optical characteristics are controlled to be identical with each other. Then, the splitted beams L1 and L2 are respectively introduced into the sample cell 52 and the cancel cell 53. Then, the transmitted beams $L_{1t}$ and $L_{2t}$ are respectively detected and photoelectrically converted into signals by the detectors 55 and 56. Then the converted signals are respectively send to lock-in amplifiers 57 and 58. The second-order differential spectra of the transmitted beams $L_{1t}$ and $L_{2t}$ are obtained by the lock-in amplifiers 57 and 58 respectively, and the second derivative spectra are respectively digitized by the AD converters 59 and 60 and then input to a computer 61. Then, the absorption spectrum of the cancel gas C is subtracted from the absorption spectrum of the sample gas G by processing the input signals with pre-memorized information, such as calculating formulae, and an absorption spectrum of the objects(impurities) can be taken. According to the above described method, it is possible to analyse impurities in the sample gas G with high precision and sensitivity. A controller for laser diode 51a, a display 62 connected to the computer 61, gas inlets 63 and 64 for the sample gas G and the cancel gas C are also shown.

However, according to the above described conventional spectroscopic method, it is important to make configurations and specifications of the sample cell 52 and the cancel cell 53 identical, and to make the two optical systems be operated under identical conditions. Thus, the cost for producing the apparatus for performing the conventional method becomes very high because of the necessary parts and components.

Therefore, there has been a strong need to develop a spectroscopic analysis method with high precision and sensitivity performed in a more compact and simple apparatus which uses a single cell system, where the single cell is once used as a sample cell for a sample gas G and then used as a cancel cell for a cancel gas C without using the conventional dual cell system having two identical cells of identical specifications and two identical optical systems operated under identical operating conditions.

When a spectroscopic analysis is performed using a single cell system by taking absorption spectra of the sample gas and the cancel gas, it is very difficult to exactly match the absorption spectra in order to calculate subtraction of the absorption spectrum of the cancel gas from that of the sample gas because the spectra are not taken at the same time but separately taken one after another.

This is because the emitting wavelength of the laser is changed due to an extremely minute change in the temperature of the laser diode while exchanging the sample gas with the cancel gas into the single cell. Further, the emitting wavelength of the laser is also changed due to the variations in the environment, such as changes in surrounding temperature, or the limitations in the effective controllable resolution of control devices between the moments of taking absorption spectra of the sample gas and the cancel gas.

Therefore, according to the spectroscopic analysis of a sample gas using the single cell system, it is very difficult to analyse objects(impurities) with high precision and sensitivity because the subtraction of the two spectra could not be exactly performed due to the difficulty in exactly matching the absorption spectra of the sample gas and the cancel gas.

In order to overcome this problem, it is known in the art to lock the wavelength of the laser diode based on the absorption spectrum of water vapor, but the measurement precision of this method is not better than that of the method using the dual cell system.

Further, to use the wavelength of the absorption spectrum of water vapor as a reference wavelength is also used in the conventional spectroscopic analysis using the single cell system. According to this method, after making the wavelength of the absorption spectrum of water vapor as a reference wavelength and marking the value of [driving current of emitting the laser diode (mA)]·[wavelength (nm)], the laser beam is drived based on this reference wavelength and the marked value, and an absorption spectrum of the object to be measured is taken from the laser beam transmitted through the single cell. However, even by this method, it is still impossible to exactly reproduce the spectra to have the same wavelength scale even by the same driving current at every time because of the minute change in the environment, such as change in surrounding temperature.

Therefore, there has been a strong need to achieve a spectroscopic analysis of high precision with a simple apparatus using single cell system.

SUMMARY OF THE INVENTION

Therefore, the present invention has been made in view of the above mentioned problem, and instead of using the dual cell system which needs precision and expensive parts and comprises two cells(a sample cell and a cancel cell) of identical specifications and dimensions, it is an object of the present invention to provide a spectroscopic method for analysing objects(impurities) in a sample gas comprising a main ingredient and the objects, both of which the absorption spectra exist in the same wavelength range, with high precision and sensitivity by using a compact and simple single cell system which uses a single cell as both of a sample cell and a cancel cell.

In accordance with an aspect of the present invention, there is disclosed a spectroscopic method for analysing objects in a sample gas using a laser beam comprising: i) a step of splitting a laser beam into a first laser beam and a second laser beam; ii) a step of transmitting said first laser beam into a sample cell where a sample gas is introduced, and measuring an intensity of a spectrum of said transmitted first laser beam ; iii) a step, being performed while performing said step ii), of transmitting said second laser beam into a reference cell where a reference gas is introduced, and measuring an intensity of a spectrum of said transmitted second laser beam, wherein said reference gas comprises an ingredient having at least two spectral lines of which wavelengths in an absorption spectrum of said reference gas are already known; and iv) a step of identifying a wavelength of objects to be measured in said sample gas by comparing said spectrum of sample gas with said spectrum of reference gas using said at least two spectral lines of said reference gas as reference wavelengths.

In accordance with another aspect of the present invention, there is disclosed a spectroscopic method for analysing objects in a sample gas using a laser beam comprising: i) a step of splitting a laser beam into a first laser beam and a second laser beam; ii) a step of transmitting said first laser beam into a sample cell where a sample gas is introduced and taking an absorption spectrum of said transmitted first laser beam, wherein said sample gas comprises a main ingredient and objects to be measured; iii) a step, being performed while performing said step ii), of transmitting said second laser beam into a reference cell where a reference gas is introduced and taking a first absorption spectrum of said transmitted second laser beam, wherein said reference gas comprises an ingredient having at least two spectral lines of which wavelengths in said first absorption spectrum are already known; iv) a step, after exhausting said sample gas out of said sample cell and introducing a cancel gas into said sample cell, of transmitting said first laser beam into said sample cell and taking an absorption spectrum of said transmitted first laser beam, wherein said cancel gas comprises only said main ingredient of said sample gas without said objects; v) a step, being performed while performing said step iv), of transmitting said second laser beam into said reference cell and taking a second absorption spectrum of said transmitted second laser beam; vi) a step of making scales of wavelength axes of all of said spectra the same by comparing a first set of absorption spectra with a second set of absorption spectra, wherein said first set comprises said absorption spectrum of said sample gas and said first absorption spectrum of said reference gas, said second set comprises said absorption spectrum of said cancel gas and said second absorption spectrum of said reference gas, and said known spectral lines of first and second spectra of said reference gas are used as references; and vii) a step of taking an absorption spectrum of said objects to be measured by subtracting said spectrum of said cancel gas from said spectrum of said sample gas, said scales of wavelength axes of said spectra of cancel gas and sample gas being made the same in said step vi).

BRIEF DESCRIPTION OF THE DRAWINGS

A further understanding of the nature and advantage of the present invention will become apparent by reference to the remaining portions of the specification and drawings.

DETAILED DESCRIPTION OF THE PREFERRED EMBODIMENT

Figure 1:
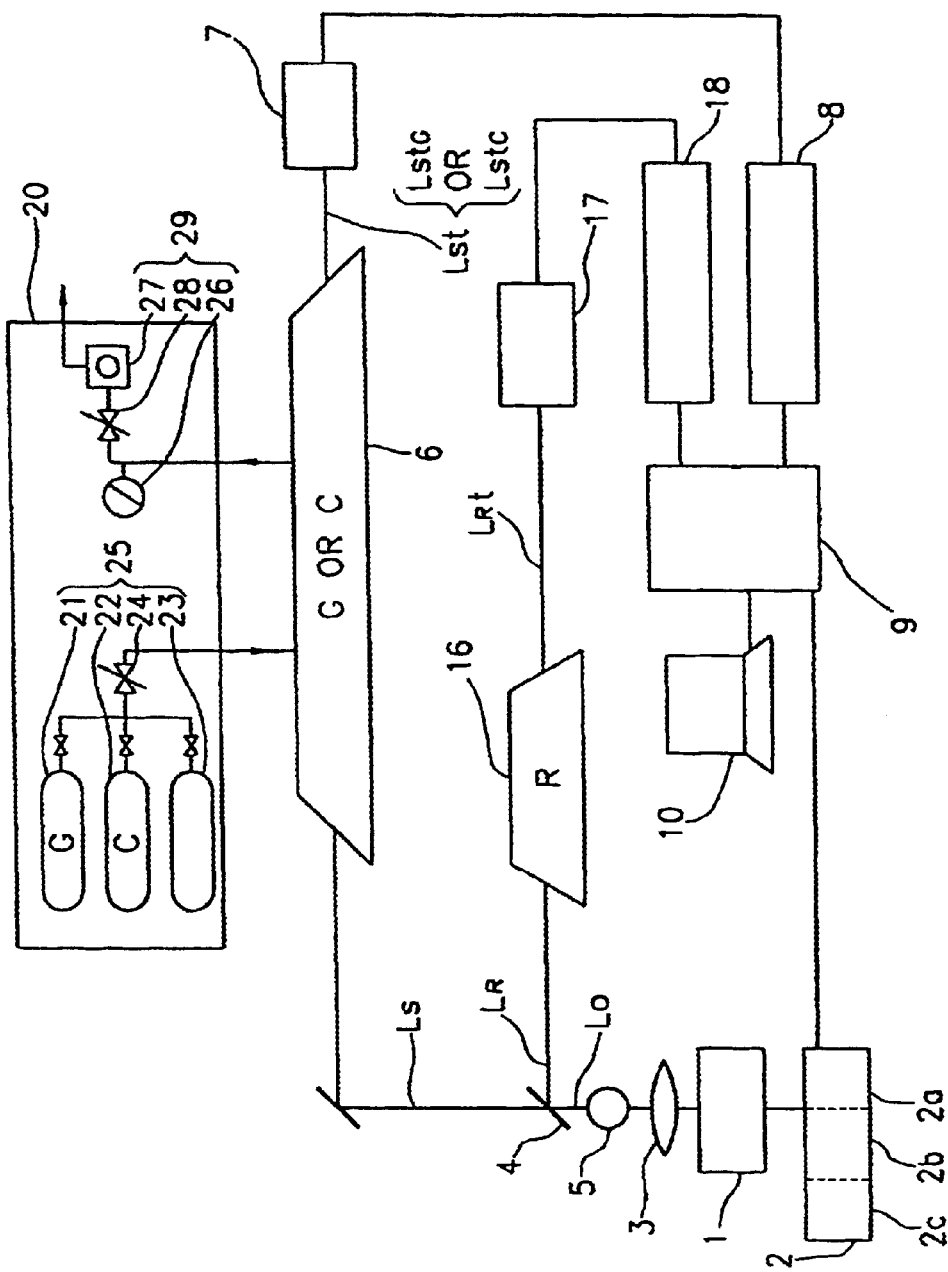
FIG. 1 is a schematic diagram of an embodiment of an apparatus for spectroscopic analysis using laser diode according to the present invention.
Figure 2:
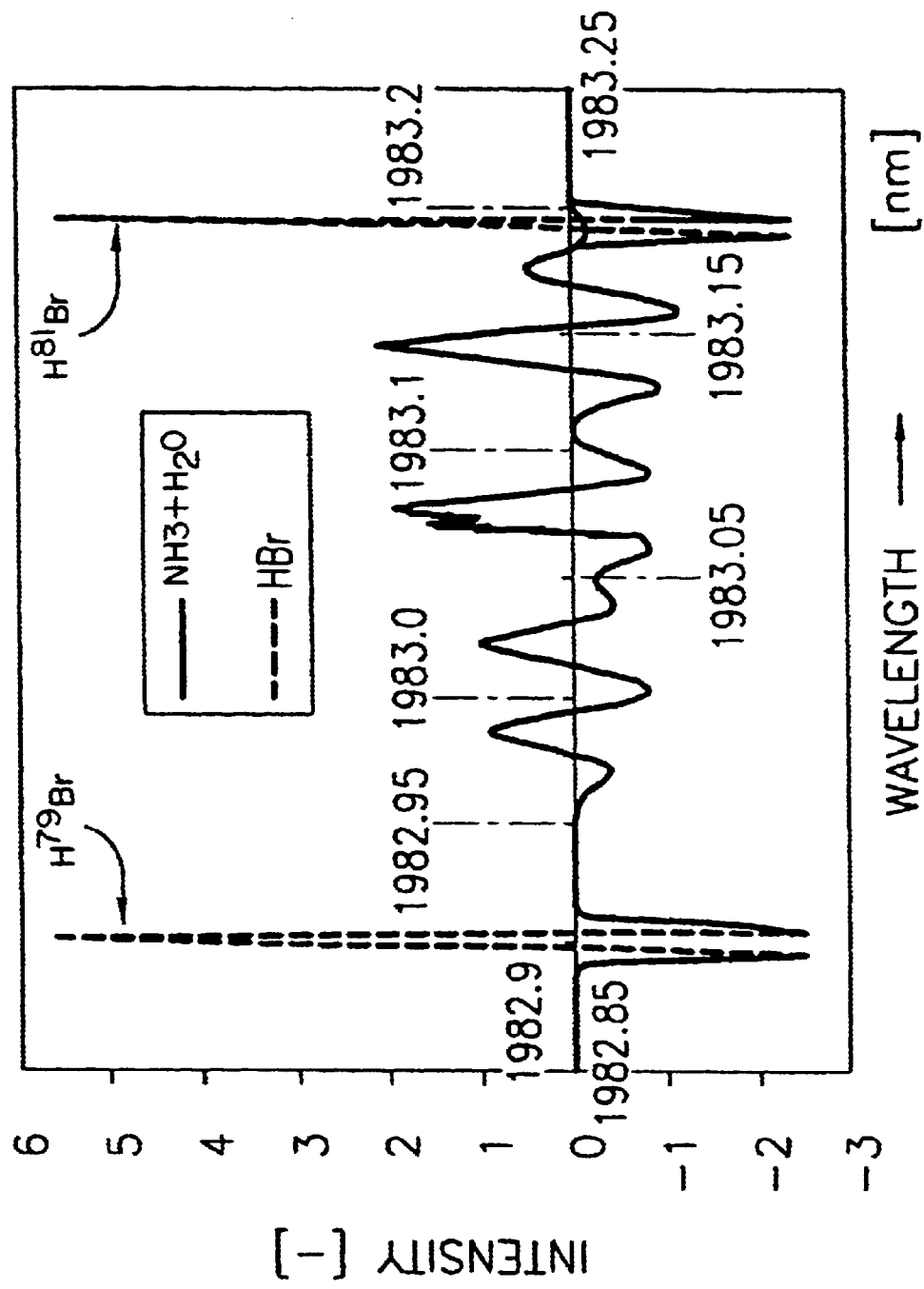
FIG. 2 is a diagram which shows absorption spectra of a sample gas(ammonia gas + water vapor) and a reference gas(hydrogen bromide) according to the present invention, the spectrum of the reference gas being simultaneously taken with the spectrum of the sample gas.

A detailed description of an embodiment according to the present invention is provided hereinafter with reference to the attached drawings of FIGS. 1 to 6. The spectroscopic method for analysing a sample gas using laser diode of the present invention is performed by an apparatus as shown in FIG. 1. FIG. 1 is a schematic diagram of an embodiment of an apparatus for spectroscopic analysis using laser diode. A laser beam having a wavelength suitable for spectroscopic analysis is emitted from a laser diode 1, which is driven by a laser controller 2. The laser controller 2 includes a temperature controller 2a for controlling temperature of a laser diode 1 to emit desired laser beam, a laser diode("LD") driver 2b for driving the laser device by applying electric currents and a function generator 2c as a modulator of emitted laser beams by wavelength modulation. Further, the laser controller 2 is coupled to a computer 9 for controlling the temperature controller 2a, the LD driver 2b and the function generator as described later in detail.

The temperature controller 2a of the laser controller 2 adjusts an operating temperature of the laser diode and the LD driver 2b continuously varies currents(DC currents) input to the laser diode so that the emitting wavelength of the laser beam varies continuously. The function generator 2c provides modulation signals(AC component) according to the wavelength modulation to the LD driver 2b. The modulation signals are superposed on the input current to the laser device, so that the emitted laser beam from the laser diode is wavelength-modulated.

In order to emit laser beams in desired wavelength range, laser diodes, such as InGaAsP, InGaAs, GaInAsSb, AlInS, AlInAs and AlGaSb, may be used as the laser diode 1, where the laser diode 1 can continuously emit in room temperature and one of them can be selected based on the desired wavelength range for analysis. Of course, laser diodes suitable for the laser diode according to the present invention are not limited to those described above, and it is sufficient for laser diodes to be used as a laser diode 1 of the present invention if they are tunable in proper wavelength ranges.

The laser beam $L_o$ thus emitted from the laser diode 1 is collimated by the collimating lens 3 and the collimated laser beam is splitted into a first laser beam $L_s$ and a second laser beam $L_R$ by a beam splitter 4. An isolator 5 may be provided as or a remover, which removes reflected and returning beams, before the beam splitter 4 in order not to make the laser beams unstable due to the returning beams reflected by the splitter 4 or some other things. The first laser beam $L_s$ is transmitted to a sample cell 6 where a sample gas G, which includes a main ingredient and objects(impurities) to be measured, and a cancel gas C consisting of the main ingredient is alternately introduced. A detector 7 receives a transmitted beam $L_{st}$ through the sample cell 6. The received transmitted beam $L_{st}$ is photoelectrically converted into electrical signals by a germanium (Ge) or an InGaAs photodiode(not shown). The electrical signals are input to a lock-in amplifier 8. The lock-in amplifier 8 outputs signals corresponding to a second derivative spectrum by processing the electrical signals, and the signals corresponding to the second derivative spectrum are input to the computer 9. The data processed by the computer 9 is displayed on a display 10.

The second laser beam $L_R$ is transmitted to a reference cell 16 where a reference gas R, of which the spectrum of the ingredients is already know in the art, is introduced. A detector 17 receives a transmitted beam $L_{Rt}$ through the reference cell 16. The received transmitted beam $L_{Rt}$ is photoelectrically converted into electrical signals by a germanium (Ge) or an InGaAs photodiode(not shown). The electrical signals are input to a lock-in amplifier 18. The lock-in amplifier 18 outputs signals corresponding to a second derivative spectrum, and the signals corresponding to the second derivative spectrum are input to the computer 9.

In the computer 9, data is memorized to control the laser controller 2 for driving the laser diode 1 to emit desired laser beams. The computer 9 sends control and operation signals to the laser controller 2 according to operating conditions of the whole system so that the laser diode 1 operates as desired.

In summary, according to the apparatus of the present invention as shown in FIG. 1, the laser controller 2 continuously varies the emission driving current applied to the laser diode 1, so that the emitting wavelength of the laser diode 1 is continuously varied and the laser beam is transmitted into the sample cell 6 where the sample gas G and the cancel gas are alternately introduced. The transmitted beam $L_{st}$, which is transmitted through the sample cell 6, is photoelectrically converted into electrical signals by the detector 7. The electrical signals are processed to be signals corresponding to a second derivative spectrum by the lock-in amplifier 8. The signals corresponding to the second derivative spectrum are input to the computer 9.

In the meantime, similar to the above description, the laser controller 2 continuously varies the emission driving current applied to the laser diode 1, so that the emitting wavelength of the laser diode 1 is continuously varied and the laser beam is transmitted into the reference cell 16 where the reference gas R having already known absorption spectrum. The transmitted beam $L_{Rt}$ which is transmitted through the reference cell 16, is photoelectrically converted into electrical signals by the detector 17. The electrical signals are processed to be signals corresponding to a second derivative spectrum by the lock-in amplifier 18. The signals corresponding to the second derivative spectrum are input to the computer 9. The data processed by the computer 9 is displayed as images on the display 10.

Further, a gas supplying unit 20 is provided for alternately introducing with proper pressure the sample gas(main ingredient M + objects m) and the cancel gas of purified main ingredients M into the sample cell 6. The gas supplying unit 20 includes a gas introducing system 25 which comprises a sample gas container 21, a cancel gas container 22 and a purge gas container 23. The containers 21, 22 and 23 are coupled to the sample cell 6 via a flow control valve 24, such as mass flow controller. The gas supplying unit 20 further includes a gas exhausting system 29 which comprises a vacuum gauge 26 and a vacuum pump 27, which is coupled to the sample cell 6 via a flow control valve 28, for purging, exhausting or controlling pressure of the sample cell 6.

The sample cell 6 may be a hollow cylinder and of which windows at the either end of the cylinder are installed at the Brewster's angle.

In the reference cell 16, the reference gas R having already known spectrum is charged with a predetermined pressure and concentrations. The wavelength of a spectral line of reference gas R is used as a reference wavelength for identifying a wavelength(or wavelengths) of objects m, or for subtracting absorption spectrum of the cancel gas from the spectrum of the sample gas. It is preferred for the reference gas R to have at lease two known spectral lines in the absorption spectrum of which the wavelength range is within the wavelength range of the spectrum of the sample gas. For example, hydrogen bromide gas or water vapor may be used as a reference gas of the present invention.

Thus, the computer receives an absorption spectrum of the transmitted laser beam $L_{StG}$ through the sample cell 6 while the sample gas G is charged in it, an absorption spectrum of the transmitted laser beam $L_{StC}$ through the sample cell 6 while the cancel gas C is charged in it and two known absorption spectra of the transmitted laser beam $L_{Rt}$ through the reference cell 16 in which the reference gas R is charged, where each of the two known absorption spectra of the reference gas R has at least two known spectral lines which will be used as references. The computer 9 performs an operation to compare first set of the absorption spectra of the sample gas G and the reference gas R with second set of the absorption spectra of the cancel gas C and the reference gas R after calibrating the scales of the wavelength axes of spectra with the spectral lines in the spectra of the reference gas R being as references. The computer 9 further performs an operation to subtract the absorption spectrum of the cancel gas C from the absorption spectrum of the sample gas G, so that the computer 9 computes intensity, abundance ratio and concentration of the absorption spectrum of the objects(impurities) in the sample gas G.

EXAMPLE

Now, an example of the according to the present invention is described hereinafter. In this example, ammonia gas $NH_3$ was used as the main ingredient M and water vapor was used as the objects(impurities) m to be measured in a sample gas G consisting of ammonia gas and water vapor.

The apparatus for spectroscopic analysis as shown in FIG. 1 was used in this example, and the configuration of the apparatus and the operating conditions were as follows.

Configuration of the Apparatus and the Operating Condition

A distributed feedback ("DFB") laser diode emitting laser beam of wavelength of 2000 nm(1980~2000 nm) was used as the laser diode 1. The input current was directly modulated by adding sine wave to it.

The sample cell 6 and the reference cell 16 were made of stainless steel and glass, respectively. The lengths of light paths through the sample cell 6 and the reference cell 16 were 50 cm and 10 cm, respectively. The windows of both cells 6 and 16 were arranged in Brewster's angle.

F InGaAs photodiodes were used as both detectors 7 and 17.

The sample gas G was consisted of ammonia gas as the main ingredient M and an extremely small quantity of water vapor as the objects(impurities) m, and was introduced into the sample cell 6 under the control of the gas supplying unit 20 with a pressure of 50 Torr and a flow rate of 40 sccm.

Purified ammonia gas without any impurity was used as the cancel gas C and introduced into the sample cell 6 under the same condition of the sample gas G.

Hydrogen bromide HBr was used as the reference gas R and the wavelengths of $H^{79}Br$(1982.9 nm) and $H^{81}Br$ (1983.2 nm) in the absorption spectrum were used as reference wavelengths.

Under the above described conditions, operations were performed as follows:

(1) Taking an absorption spectrum of the sample gas ($NH_3+H_2O$) G

After introducing the sample gas G into the sample cell 6, the first laser beam $L_s$ splitted from the laser beam $L_o$ from the laser diode 1 was transmitted to the sample cell 6. Then, the detector 7 detected the transmitted beam $L_{StG}$ through the sample cell 6 to take an absorption spectrum of the sample gas G.

In the meantime, the second laser beam $L_R$ was transmitted to the reference cell 16 where the reference gas(HBr) R, which has two known wavelengths in the absorption spectrum lying in the same wavelength range with the absorption spectrum of the sample gas G, was introduced under the above described condition. The detector 17 detected the transmitted beam $L_{Rt}$ through the reference cell 16.

Further, the detected beams $L_{StG}$ and $L_{Rt}$ by the detectors 7 and 17 were respectively input to the lock-in amplifiers 8 and 18 to be processed for producing second derivative spectra. The data of the second derivative spectra were input to the computer 9. The computer 9 compared the spectrum of the sample gas G with that of the reference gas R. Then, wavelengths in the absorption spectrum of the sample gas G were identified and computed by using the known wavelengths of the hydrogen bromide as reference wavelengths in the computer 9. Referring FIG. 2 again, the two spectra of the sample gas G and the reference gas R are shown as overlapped.

(2) Taking an absorption spectrum of the cancel gas ($NH_3$)C

After exhausting the sample gas G out of the sample cell 6, the sample cell 6 was purged by flowing highly purified nitrogen gas and vacuum pumping. Then, the cancel gas C consisting solely of the main ingredient($NH_3$) of the sample gas G was introduced into the sample cell 6. Then, as before, the first and second laser beam $L_s$ and $L_R$ were respectively transmitted to the sample cell 6 and the reference cell 16 where the reference gas(HBr) R was maintained.

Then, the detectors 7 and 17 respectively detected the transmitted beam $L_{StG}$ and $L_{Rt}$ through the sample cell 6 and the reference cell 16.

Further, the detected beams $L_{StG}$ and $L_{Rt}$ by the detectors 7 and 17 were respectively input to the lock-in amplifiers 8 and 18 to be processed for producing second derivative spectra. The data of the second derivative spectra were input to the computer 9. The computer 9 compared the spectrum of the cancel gas C with that of the reference gas R. Then, wavelengths in the absorption spectrum of the cancel gas C were identified and computed by using the known wavelengths of the hydrogen bromide as reference wavelengths in the computer 9. Referring FIG. 3 again, the two spectra of the cancel gas C and the reference gas R are shown as overlapped.

(3) The absorption spectra of the sample gas G and the cancel gas C were revised by using the spectra of the reference gas R as references so that the scales of wavelength axes of all spectra were made to be the same.

The spectra of the sample gas G and the cancel gas C were calibrated by the data taken in the above described steps (1) and (2) so that the scales of wavelength axes of all spectra were made to be the same. As clearly shown by comparing FIG. 2 with FIG. 3, since the distance between the spectral lines of the reference gas R in the spectrum shown in FIG. 2 was shorter than that shown in FIG. 3, the scales of the spectra shown in FIG. 2 was calibrated according to those shown in FIG. 3, or vice versa. Referring to FIG. 4, there are shown the absorption spectra of the sample gas G and the reference gas R after calibration. It can be seen that the scales of all spectra were made to be the same.

(4) Taking an absorption spectrum of the objects (impurities) m to be measured by subtracting the spectrum of the cancel gas C from that of the sample gas G.

Figure 3:
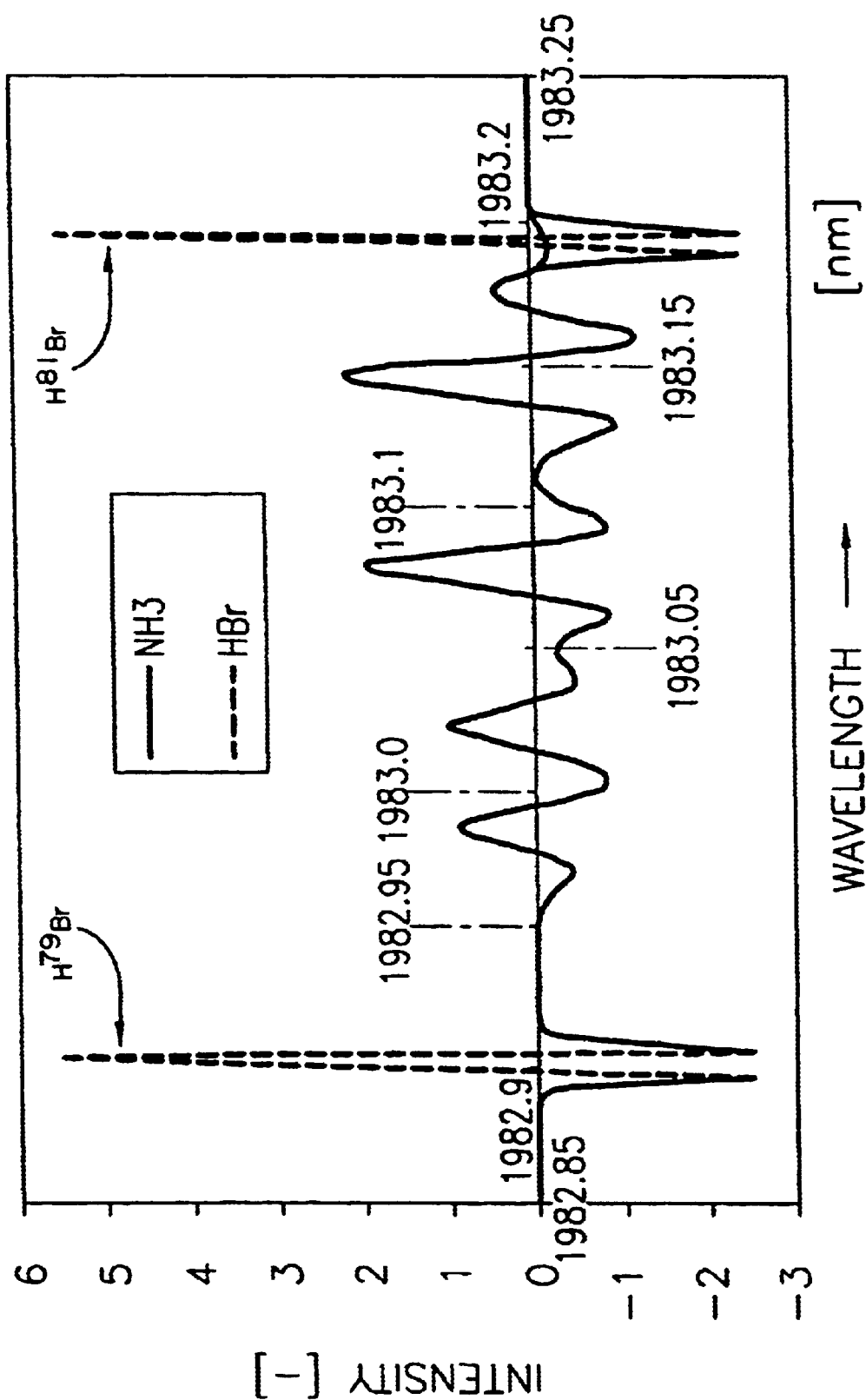
FIG. 3 is a diagram which shows absorption spectra of a cancel gas(ammonia gas) and a reference gas(hydrogen bromide) according to the present invention, the spectrum of the reference gas being simultaneously taken with the spectrum of the cancel gas.
Figure 4:
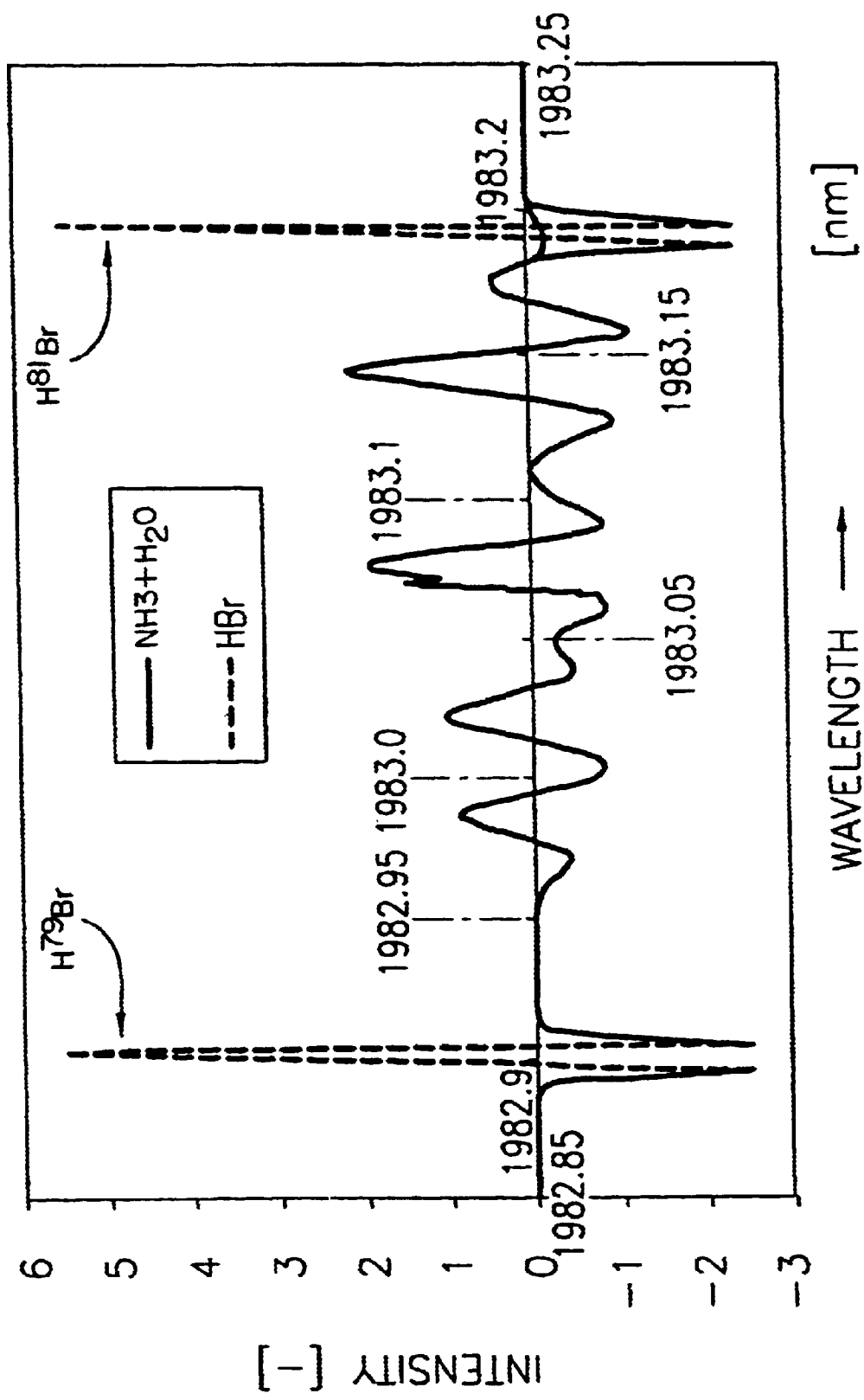
FIG. 4 is a diagram which shows calibrated spectra of those shown in FIG. 2 according to scales of the spectra shown in FIG. 3.
Figure 5:
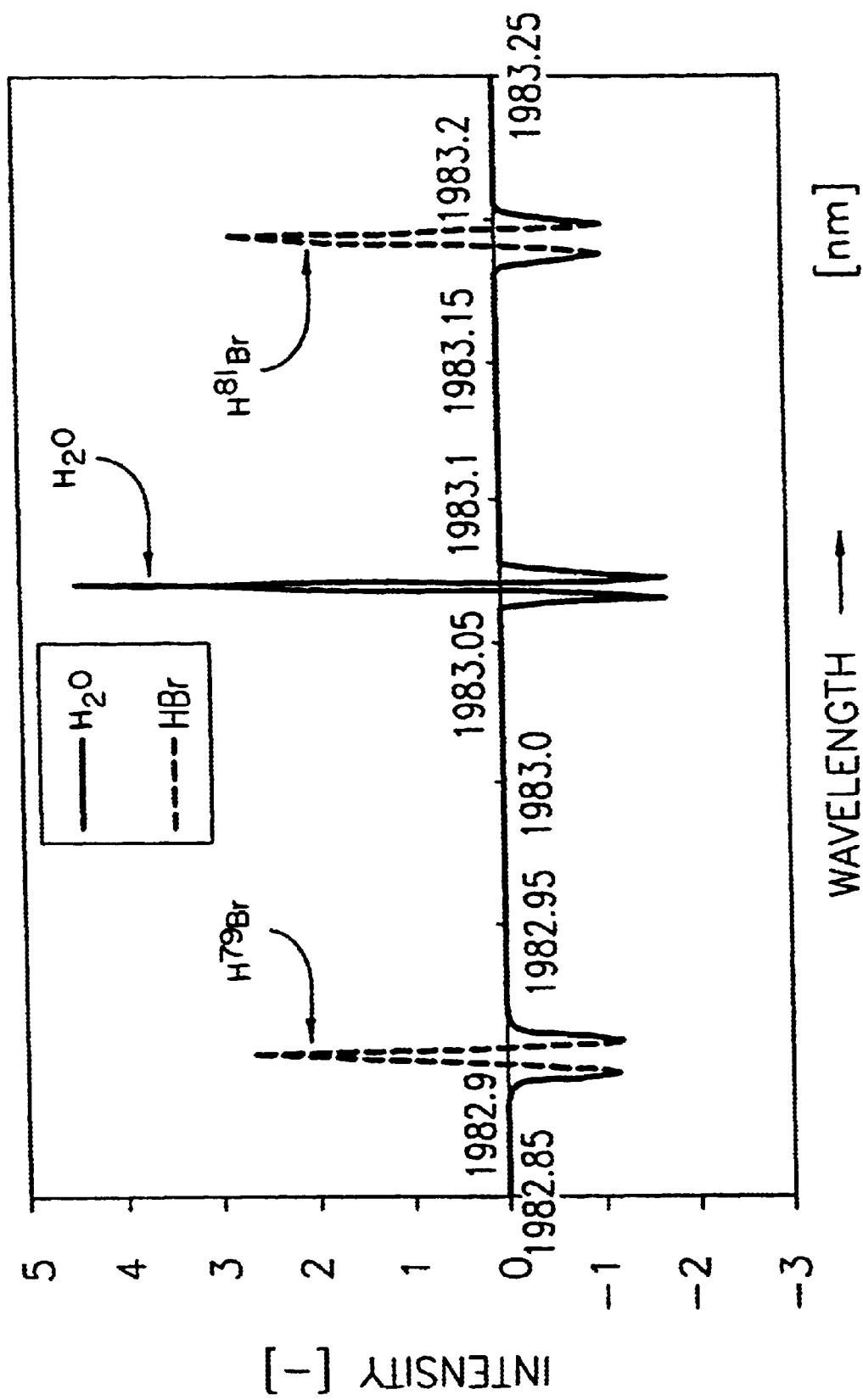
FIG. 5 is a diagram which shows an absorption spectrum of an object(water vapor) to be measured and a reference gas(hydrogen bromide) taken by subtracting the absorption spectrum of a cancel gas(ammonia gas) shown in FIG. 3 from the absorption spectrum of a sample gas(ammonia gas + water vapor) shown in FIG. 2.
Figure 6:
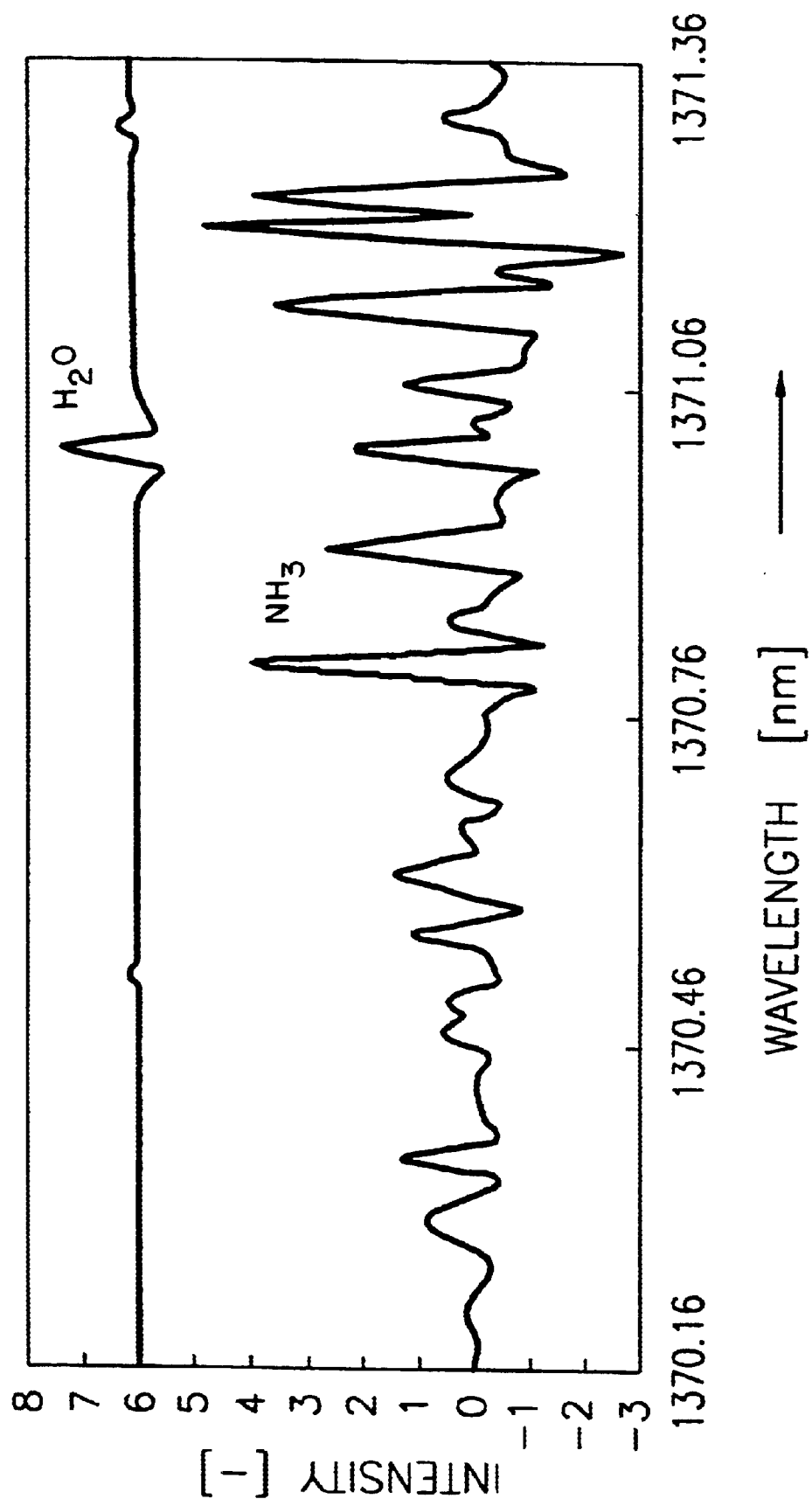
FIG. 6 is a diagram which shows absorption spectra of ammonia($NH_3$) and water vapor($H_2O$).
Figure 7:
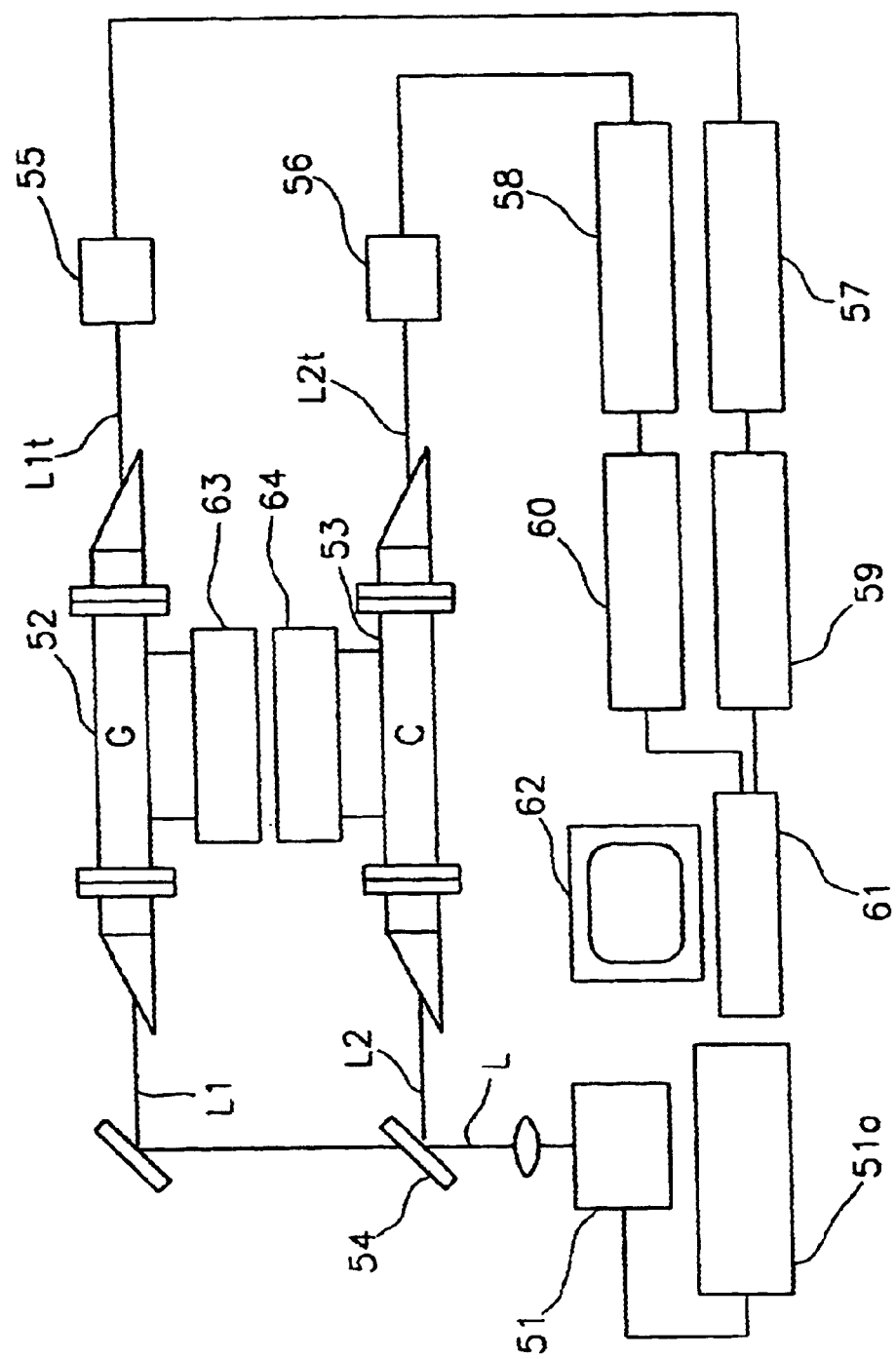
FIG. 7 is a schematic diagram of an example of a conventional apparatus for spectroscopic analysis using dual cell system.

An absorption spectrum of water vapor $H_2O$, the objects (impurities) to be measured, was taken through operations of the computer 9 for comparing the calibrated absorption spectrum of the sample gas G shown in FIG. 4 with the absorption spectrum of the cancel gas C shown in FIG. 3 and subtracting the absorption spectrum of the cancel gas C from the absorption spectrum of the sample gas G. The absorption spectrum of the water vapor, the object m to be measured, thus produced is shown in FIG. 5.

(5) Calculating the concentration of the objects(impurities) $H_2O$) m to be measured in the sample gas G It was very easy to calculate the abundance ratio of the objects(impurities) m in the sample gas G by measuring the intensity of the absorption spectrum of the objects taken in the above described step (4) and comparing the measured intensity with a pre-memorized data of a relationship of concentrations to intensities.

Further, in the above example, the hydrogen bromide was used as the reference gas R, where the hydrogen bromide has two known spectral lines of $H^{79}Br$(1982.9 nm) and $H^{81}Br$ (1983.2 nm) in the absorption spectrum. However, those skilled in the art will readily notice that it is possible to use any gas or any mixture of gases which has at least two spectral lines of known wavelengths in the absorption spectrum, between which the absorption spectrum of the objects to be measured lies, as a reference gas R.

Further, although it is described in the above example to measure a very small quantity of water vapor in an ammonia gas, it is also possible to measure with high precision and sensitivity a extremely small quantity of impurities(e.g. water vapor) in a sample gas(e.g. silane $SiH_4$), where an absorption spectrum of the impurities lies in a wavelength range of an absorption spectrum of the sample gas.

Note that, according to the present invention, it is still possible to measure impurities in nitrogen gas, oxygen gas, argon gas or semiconductor gas, where the absorption spectrum of the impurities does not lie in a wavelength range of an absorption spectrum of one of the above gases.

According to the present invention, it is possible to achieve following advantages:

A laser beam is splitted into a first laser beam and a second laser beam, and then the splitted laser beams are respectively transmitted into a sample cell and a reference cell. Particularly, the first laser beam is transmitted into the sample cell once while a sample gas is in the sample cell and again while a cancel gas is in the sample cell. The sample gas is consisted of a main ingredient and impurities and the cancel gas is consisted solely of the main ingredient of the sample gas. Then, the laser beams transmitted through the cells are simultaneously detected by corresponding beam detectors, respectively. Therefore, it is possible to take absorption spectra of the sample gas and the reference gas where the spectral lines of known wavelengths of the reference gas are overlapped on the spectrum of the sample gas, and then it is also possible to take absorption spectra of the cancel gas and the reference gas where the spectral lines of known wavelengths of the reference gas are overlapped on the spectrum of the cancel gas. By comparing the two sets of the absorption spectra, the scales of the wavelength axes of one set of spectra is calibrated by that of the other set of spectra, so that the scales of the wavelength axes of all spectra are made to be the same. By this calibrating, it is possible to precisely determine the difference between the two sets of spectra.

Further, since the reference gas has at least two spectral lines of known wavelengths in the spectrum, it is possible to perform wavelength scanning of the laser diode beam based on the know wavelengths as references.

Further, since it is possible to take absorption spectra of the sample gas and the cancel gas on which the spectrum of the reference gas are respectively overlapped, it is possible to respectively calibrate the scales of the spectra based on the scales of the spectra of the reference gas, and eventually the scales of all spectra may be made to be the same.

As a result, according to the present invention, it is possible to perform a subtraction of the absorption spectra and to perform spectroscopic analysis of an extremely small quantity of impurities (objects to be measured) with high precision and sensitivity.

Therefore, according to the present invention, it is possible to analyse with high precision and sensitivity an extremely small quantity of impurities in a sample gas with a very simple apparatus using single cell system without complex, expensive and difficult to operate dual cell system.

Although the preferred embodiment of the present invention has been disclosed for illustrative purposes, those skilled in the art will appreciate that various modifications, additions and substitutions are possible, without departing from the scope and the spirit of the present invention as disclosed in the accompanying claims.

What is claimed is:

1. A spectroscopic method for analysing objects in a sample gas using a laser beam comprising:

i) a step of splitting a laser beam into a first laser beam and a second laser beam;

ii) a step of transmitting said first laser beam into a sample cell where a sample gas is introduced, and measuring an intensity of a spectrum of said transmitted first laser beam;

iii) a step, being performed while performing said step ii), of transmitting said second laser beam into a reference cell where a reference gas is charged, and measuring an intensity of a spectrum of said transmitted second laser beam, wherein said reference gas comprises an ingredient having at least two spectral lines of which wavelengths in an absorption spectrum of said reference gas are already known in the same wavelength range with the absorption spectrum of said sample gas; and iv) a step of identifying a wavelength of objects to be measured in said sample gas by comparing said spectrum of sample gas with said spectrum of reference gas using said at least two spectral lines of said reference gas as reference wavelengths.

2. A spectroscopic method for analysing objects in a sample gas using a laser beam as claimed in claim 1, wherein said reference gas is a hydrogen bromide gas comprising $H^{79}Br$ and $H^{81}Br$.

3. A spectroscopic method for analysing objects in a sample gas using a laser beam as claimed in claim 1, wherein each of wavelengths of said at least two spectral lines of said reference gas are near from a wavelength range of said spectrum of said sample gas, and a peak in said spectrum of said object to be measured lies between said at least two spectral lines of said reference gas.

4. A spectroscopic method for analysing objects in a sample gas using a laser beam as claimed in claim 3, wherein said reference gas is a hydrogen bromide gas comprising $H^{79}Br$ and $H^{81}Br$.

5. A spectroscopic method for analysing objects in a sample gas using a laser beam comprising;

i) a step of splitting a laser beam into a first laser beam and a second laser beam;

ii) a step of transmitting said first laser beam into a sample cell where a sample gas is introduced and taking an absorption spectrum of said transmitted first laser beam, wherein said sample gas comprises a main ingredient and objects to be measured;

iii) a step, being performed while performing said step ii), of transmitting said second laser beam into a reference cell where a reference gas is introduced and taking a first absorption spectrum of said transmitted second laser beam, wherein said reference gas comprises an ingredient having at least two spectral lines of which wavelengths in said first absorption spectrum are already known;

iv) a step, after exhausting said sample gas out of said sample cell and introducing a cancel gas into said sample cell, of transmitting said first laser beam into said sample cell and taking an absorption spectrum of said transmitted first laser beam, wherein said cancel gas comprises only said main ingredient of said sample gas without said objects;

v) a step, being performed while performing said step iv), of transmitting said second laser beam into said reference cell and taking a second absorption spectrum of said transmitted second laser beam;

vi) a step of making scales of wavelength axes of all of said spectra the same by comparing a first set of absorption spectra with a second set of absorption spectra, wherein said first set comprises said absorption spectrum of said sample gas and said first absorption spectrum of said reference gas, said second set comprises said absorption spectrum of said cancel gas and said second absorption spectrum of said reference gas, and said known spectral lines of first and second spectra of said reference gas are used as references; and vii) a step of taking an absorption spectrum of said objects to be measured by subtracting said spectrum of said cancel gas from said spectrum of said sample gas, said scales of wavelength axes of said spectra of cancel gas and sample gas being made the same in said step vi).

6. A spectroscopic method for analysing objects in a sample gas using a laser beam as claimed in claim 5, wherein said sixth step is a step of calibrating said wavelength axes of all of said spectra by matching said reference wavelengths of said first spectrum of said reference gas with those of said second spectrum of said reference gas.

7. A spectroscopic method for analysing objects in a sample gas using a laser beam as claimed in claim 5, wherein said reference gas is a hydrogen bromide gas comprising $H^{79}Br$ and $H^{81}Br$.

8. A spectroscopic method for analysing objects in a sample gas using a laser beam as claimed in claim 5, wherein each of wavelengths of said at least two spectral lines of said reference gas are near from a wavelength range of said spectrum of said sample gas, and a peak in said spectrum of said object to be measured lie between said at least two spectral lines of said reference gas.

9. A spectroscopic method for analysing objects in a sample gas using a laser beam as claimed in claim 8, wherein said reference gas is a hydrogen bromide gas comprising $H^{79}Br$ and $H^{81}Br$.

* * * * *